US00RE41366E

(19) United States
(12) Reissued Patent
Thal et al.

(10) Patent Number: US RE41,366 E
(45) Date of Reissued Patent: Jun. 1, 2010

(54) TOTAL SYNTHESIS OF GALANTHAMINE, ANALOGUES AND DERIVATIVES THEREOF

(75) Inventors: Claude Thal, Sceaux (FR); Catherine Guillou, Gif-sur-Yvette (FR); Jean-Luc Beunard, Orsay (FR); Emmanuel Gras, Rochefort (FR); Pierre Potier, Paris (FR)

(73) Assignee: Centre National del la Recherche Scientifique (CNRS) (FR)

(21) Appl. No.: 12/283,904

(22) PCT Filed: Jun. 14, 2002

(86) PCT No.: PCT/FR02/02045

§ 371 (c)(1),
(2), (4) Date: May 10, 2004

(87) PCT Pub. No.: WO02/102803

PCT Pub. Date: Dec. 27, 2002

Related U.S. Patent Documents

Reissue of:
(64) Patent No.: 7,109,327
Issued: Sep. 19, 2006
Appl. No.: 10/480,722
Filed: May 10, 2004

(30) Foreign Application Priority Data

Jun. 15, 2001 (JP) ..... 0107859

(51) Int. Cl.
*C07D 491/04* (2006.01)
*C07D 493/10* (2006.01)
*C07D 311/96* (2006.01)
*C07D 307/91* (2006.01)
*C07D 317/72* (2006.01)

(52) U.S. Cl. ..... 540/519; 546/65; 546/110; 549/265; 549/342; 549/358; 549/399; 549/446; 549/458

(58) Field of Classification Search ..... 540/519; 546/65, 110; 549/265, 342, 358, 399, 446, 549/458

See application file for complete search history.

(56) References Cited

PUBLICATIONS

A. L. Harvey, "The Pharmacology of Galanthamine and its Analogues", Pharmac. Ther. vol. 68, No. 1, pp. 113–128, 1995.*

Weinstock, "Selectivity of Cholinesterase Inhibition, Clinical Implications for the Treatment of Alzheimer's Disease", CNS Drugs Oct. 12, 1999 (4), pp. 307–323.*

Barton et al., "Phenol Oxidation and Biosynthesis. Part V. The Synthesis of Galanthamine", J. Chem. Soc. (1962), pp. 806–817.*

Czollner et al., "New Kilogram–Synthesis of the Anti–Alzheimer Drug (–)–Galathamine", Tetrahedron Letters 39 (1998), pp. 2087–2088.*

Krikorian et al., "New Achievements in the Field of Intramolecular Phenolic Coupling Reactions, Using Hypervalent (III) Iodine Reagent: Synthesis of Galanthamine", Synthetic Communications, 30(16), 2833–2846 (2000), pp. 2833–2846.*

Ishizaki et al., "Synthetic Approaches toward Spiro[2, 3–dihydro–4*H*–1–benzopyran–4,1'–cyclohexan]–2–one Derivatives via Radical Reactions: Total Synthesis of (±)–Lycoramine", J. Org. Chem. 1993, 58, 3877–3885.*

Gras et al., "A formal sythesis of (±O lycoramine via an intramolecular Heck reaction", Tetrahedron Letters 40 (1999), pp. 9243–2944.*

Trost et al., "Enantioselective Total Synthesis of (–)–Galanthamine", J. Am. Chem. Soc. 2000, 122, pp. 11262–11263.*

Pilger et al., "A New Stereoselective Approach Towards the Galanthamine Ring System via an Intramolecular Heck Reaction", Synlett 2000, No. 8, pp. 1163–1165.*

Parsons et al., "A general approach to the galanthamine ring system", Tetrahedron Letters 42 (2001), pp. 2209–2211.*

T. G. Back, "Dehydrogenation of Hydrazines and of 4–Azacholestan–3–one with Benzenseleninic Acid and Benzeneseleninic Anhydride", J.C.S. Chem. Comm., 1978 (pp. 278–279).*

Barton et al., "Dehydrogenation of Steroidal and Triterpenoid Ketones using Benzene–seleninic Anhydride", J.C.S.Perkin I (1980), pp. 2209–2212.*

Barton et al., "Dehydrogenation of Lactones using Benzeneseleninic Anhydride", J. Chem. Soc. Perkin Trans. I, 1982, pp. 1919–1922.*

Barton et al., "A Practical Catalytic Method for the Preparation of Steroidal 1,4–Dien–3–ones by Oxygen Atom Transfer from Iodoxybenzene to Diphenyl Di–selende", J. Chem. Soc. Perkin Trans. I, 1982, pp. 1947–1952).*

* cited by examiner

*Primary Examiner*—Bruck Kifle
(74) *Attorney, Agent, or Firm*—Lerner, David, Littenberg, Krumholz & Mentlik, LLP

(57) ABSTRACT

The invention relates to a method for the synthesis of galanthamine, the derivatives and analogues thereof of formula (1) where $R_1$=a hydrogen atom, $R_2$=a hydroxy group, $R_1$ and $R_2$ together form =O, $R_3$, $R_4$, and $R_5$ independently=a hydrogen atom, a hydroxy group or a $(C_1–C_2)$alkoxy group, $R_6$=H, $(C_1–C_{12})$alkyl, $(CH_2)_n NR_7R_8$, or $—(CH_2)_nN^+R_7R_8R_9$ where n=1 to 12, Z=two hydrogen atoms, or an oxygen atom and X=an oxygen, sulphur or nitrogen atom, or a —SO, $—SO_2$, or $—NR_6$ group where $R_6$ is as defined above or is an amine protecting group.

(1)

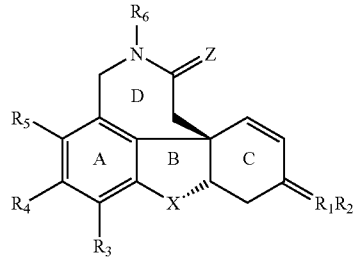

17 Claims, No Drawings

TOTAL SYNTHESIS OF GALANTHAMINE, ANALOGUES AND DERIVATIVES THEREOF

Matter enclosed in heavy brackets [ ] appears in the original patent but forms no part of this reissue specification; matter printed in italics indicates the additions made by reissue.

The present patent application is a non-provisional application of International Application No. PCT/FR02/02045, filed Jun. 14, 2002.

The present invention relates to a method of synthesizing galanthamine, its analogues, and its derivatives, and to the corresponding synthesis intermediates.

(−)-Galanthamine of formula (A)

(A)

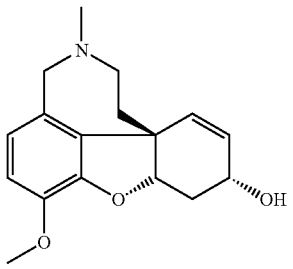

is an alkaloid which is isolated from the family of the Amaryllidaceae and acts as a competitive, selective, and reversible inhibitor of acetylcholinesterase (Harvey A. L. (1995), Pharmac. Ther, 68, 113).

It has been used for a number of years in the treatment of myasthenia and in certain neurological diseases such as poliomyelitis, as an anticurare agent, and as a parasymphaticomimetic agent.

In particular this compound enhances the cognitive functions of persons suffering from Alzheimer's disease, which is characterized by damage to the cholinergic neurotransmission (Weinstock M. (1999), CNS Drugs, 12, 307). At present galanthamine is sold for this indication in Austria and Sweden and should shortly be so sold in the other countries of Europe and in the United States.

(−)-Galanthamine may be extracted from a variety of plant sources, in particular from Galanthus nivalis, G. narcissus, G. leucojum or G. crinium, but in very small quantities, which are inadequate for commercial use.

Galanthamine was first synthesized by Barton D. H. R. et al. (J. Chem. Soc. (1962), 806), the key step of this method being the oxidative cyclization of the phenol, of which the yield is only 0.5%. Many groups have attempted to improve the yields of this synthesis method so as to allow it to be used on the industrial scale; thus Czollner L. et al. (Tetrahedron Letters (1998), 39, 2087) obtained a yield of 45 to 50% and Krikorian et al. (Synthetic Communications (2000), 30 (16), 2833) yields of 60%. However, despite the increase in these yields, these methods remain difficult to implement on the industrial scale.

Furthermore, a number of groups have attempted to develop syntheses of galanthamine, its analogues and derivatives by nonbiomimetic routes.

Thus the group of Ishisaki M. et al. (J. Org. Chem. (1993), 58, 3877) describes a synthesis by free-radical reaction of lycoramine, an alkaloid from the galanthamine family. Following a retrosynthetic analysis of lycoramine (1,2-dihydrogalanthamine), the authors show that the compound of structure (B)

(B)

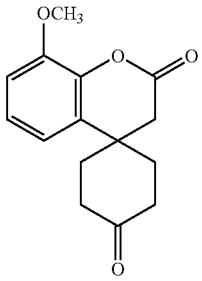

is able to lead only to the total synthesis of lycoramine, in 3 steps with an overall yield of 13%.

This intermediate therefore does not make it possible to obtain galanthamine.

Galanthamine and its derivatives such as lycoramine are characterized by the presence of a spiro quaternary carbon, the creation of which has been found to be the limiting step in the total synthesis.

The inventors were the first to describe a new strategy to form this critical quaternary carbon in lycoramine (Gras E. et al., Tetrahedron Letters (1999), 40, 9243), using an intramolecular Heck reaction; they synthesized the intermediate of formula (C)

(C)

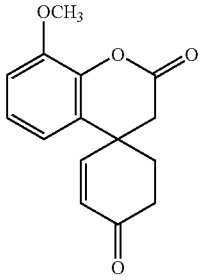

and used it to prepare lycoramine by introduction of an amine group, Pictet-Spengler cyclization, and reduction with $LiAlH_4$ in tetrahydrofuran in accordance with the technique described by Ishisaki M. (reference already cited).

More recently Trost B. M. et al. (J. Am. Chem. Soc. (2000), 122 (45), 11262) have described the first full enantioselective synthesis of (−)-galanthamine without using the oxidative coupling of the phenol: they perform a cyclization by an intramolecular Heck reaction in the presence of a bidentate alkylphosphine ligand and a palladium catalyst.

This synthesis, however, is made up of 15 steps and its overall yield is 1%.

Pilger C. et al. (Synlett (2000), 8, 1163) and Parsons P. J. et al. (Tetrahedron Letters, (2001), 42, 2209) have likewise described new synthetic pathways for the skeleton of 3-deoxygalanthamine, using a selective intramolecular Heck reaction as the key step. This approach does not allow creation of the allyl function, which is essential for the biological activity.

In view of the importance of the market for galanthamine, its derivatives, and its analogues, it is absolutely indispensable to develop a synthesis which is easy, rapid, and economically viable.

The inventors have now found, surprisingly, that by using an oxidizing agent mixed with a support, and starting from the compound of formula (C) or an analogue, they obtained galanthamine or its derivatives in conditions which are compatible with an industrial utilization.

The invention accordingly provides a method of synthesizing compounds of formula (1)

(1)

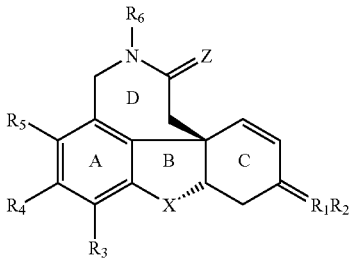

in which either $R_1$ represents a hydrogen atom and $R_2$ represents a hydroxyl group, or $R_1$ and $R_2$ together form =O, $R_3$, $R_4$ and $R_5$ represent each independently of one another a hydrogen atom, a hydroxyl group or a $(C_1–C_{12})$ alkoxy group, R6 represents a hydrogen atom, a $(C_1–C_{12})$alkyl group, a group $—(CH^2)_nNR_7R_8$ or a group $—(CH_2)_nN^+R_7R_8R_9$ where n=1 to 12, $R_7$ and $R_8$ represent each independently of one another a hydrogen atom; a cyano; $(C_1–C_4)$alkyl; aryl $(C_1–C_4)$alkyl; aryl$(C_1–C_4)$alkenyl; $(C_1–C_4)$alkyl-carbonyl or arylcarbonyl radical; the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals; or $R_7$ and $R_8$ are linked to each other and form, together with the nitrogen atom to which they are attached, a heterocycle; and $R_9$ represents a hydrogen atom or a cyano, $(C_1–C_4)$alkyl, aryl$(C_1–C_4)$alkyl, aryl$(C_1–C_4)$ alkenyl, alkylcarbonyl or arylcarbonyl radical, the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals;

Z represents either two hydrogen atoms or one oxygen atom, and

X represents alternatively an oxygen atom or a sulfur atom or a nitrogen atom or an —SO group or an $—SO_2$ group or a group $—NR_6$ where $R_6$ is as defined above or represents an amine-protective group, characterized in that it comprises a step in which an α,β-ethylenic ketone of formula (10)

(10)

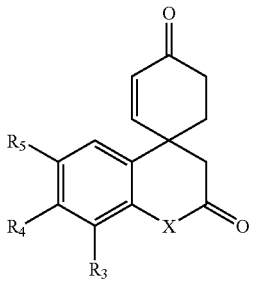

is oxidized to a spirodienone of formula (11), (11)

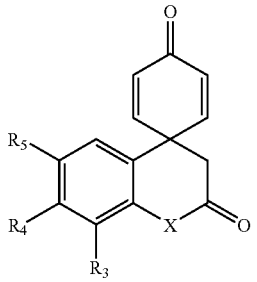

In one advantageous embodiment of the method the support is a mixture of silica and alumina.

In one particularly advantageous embodiment the mixture of silica and alumina is a 50/50 mixture.

In one preferred embodiment the oxidation is performed in the presence of benzeneselinic anhydride mixed with a support, preferably an inorganic support. By way of example mention may be made in particular of molecular sieves whose size is preferably between 3 and 5 Å, and silica/alumina mixtures.

The compounds of formula (1) are analogues and derivatives of galanthamine, particularly basic analogues of galanthamine in which the nitrogen atom of the ring D can be converted to its salt form, and analogues containing an iminium function in the ring D, such as those described in international application WO 97/03987 and in the article by Mary A. et al. (Bioorganic and Medicinal Chemistry (1988), 6, 1835). These compounds possess 3 asymmetric carbons and may therefore exist in the form of pure stereoisomers or mixtures. Preferably the 3 carbon is of α configuration as in natural galanthamine.

In one advantageous embodiment of the method according to the invention a derivative of formula (6)

(6)

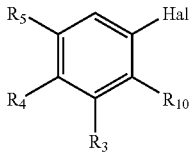

in which Hal represents a halogen atom selected from bromine and iodine atoms, $R_3$, $R_4$, and $R_5$ are as defined in claim 1, and $R_{10}$ represents an amine group or a hydroxyl group is reacted with (1,4-dioxaspiro[4.5]dec-7-en-8-yl) acetic acid of formula (7), (7)

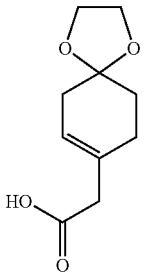

and a compound of formula (8)

(8)

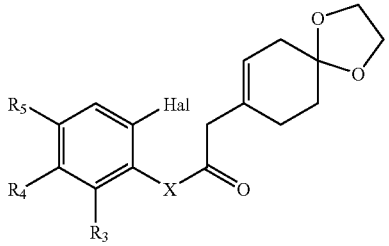

is obtained which is cyclized by an intramolecular Heck reaction to give a compound of formula (9)

(9)

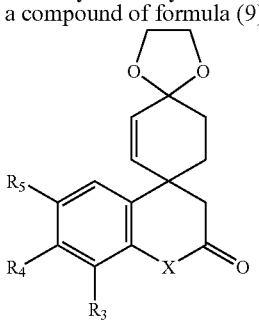

the cyclization reaction is performed under conventional conditions known to the skilled worker, particularly in the presence of a palladium catalyst or a palladium(0) precursor catalyst, such as for example tris(dibenzylideneacetone) dipalladium, and bidentate alkylphosphine derivatives such as for example 1,2-bis-(diphenylphosphino)ethane (dppe) or 1,2-bis(dicyclohexylphosphino)ethane (dcpe), and in a mixture of thallium acetate and acetonitrile or dimethylacetamide; subsequently the dioxolane function of the compound of formula (9) is deprotected, in the presence for example of a hydride acceptor such as, for example, triphenylcarbenium tetrafluoroborate or triphenylcarbenium hexafluorophosphate, to give the α,β-ethylenic ketone of formula (10)

(10)

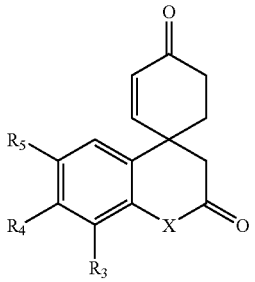

which is oxidized in the presence of benzeneseleninic anhydride, to which a mixture, preferably 50/50, of silica and alumina has been added, to give a compound of formula (11)

(11)

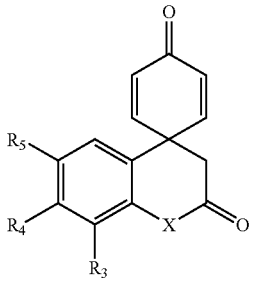

in which $R_3$, $R_4$, and $R_5$ and X are as defined above; subsequently the amine group is introduced into said compound of formula (11) by opening the lactone with an amine of formula $NHR_6$ where $R_6$ is as defined above; this reaction is accompanied by a spontaneous, Michael-type addition reaction of the intermediately generated phenol with the dienone to form, with a quantitative yield, the corresponding amide of formula (12)

(12)

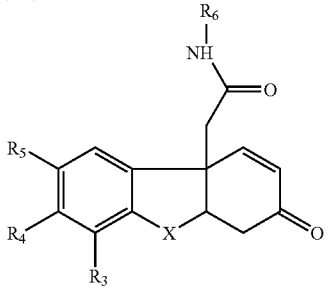

in which $R_3$, $R_4$, $R_6$ and X are as defined above.

Subsequently, the amide of formula (12) is cyclized, for example by a Pictet-Spengler-type reaction; said reaction may be performed in the presence of paraformaldehyde and trifluoroacetic acid; this gives a compound of formula (1a)

(1a)

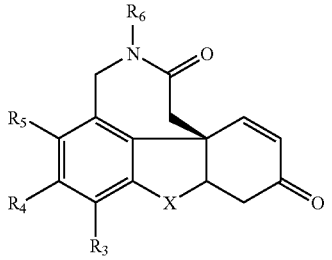

whose diastereoselective reduction, for example with L-Selectride®, leads to the corresponding derivative of formula (1b)

(1b)

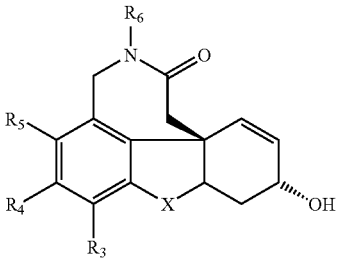

which is itself reduced under conventional conditions to give the final, corresponding compound of formula (1c)

(1c)

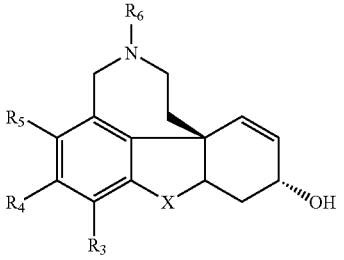

According to another embodiment of the invention, when it is desired to obtain optically active compounds of formula (1a) to (1c), the compound (12) or (1a) is subjected to resolution under conventional conditions known to the skilled worker, and the steps described above are conducted.

In one particularly advantageous embodiment of the invention the method allows galanthamine to be obtained in the form of the racemate or of its optically pure isomers.

The method according to the invention allows galanthamine, its analogues, and its derivatives to be obtained within a reasonable number of steps which are compatible with an industrial process.

The invention likewise provides compounds of formula (11) and (12)

(11)

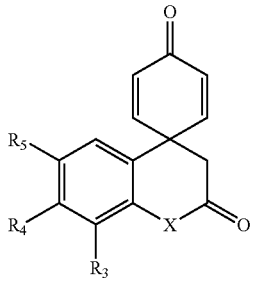

(12)

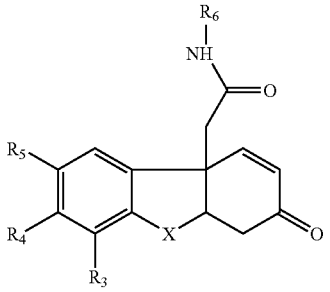

in which $R_3$, $R_4$, $R_5$, $R_6$, and X are as defined above, which are useful as synthesis intermediates.

The invention further provides compounds of formula (8) and (9)

(8)

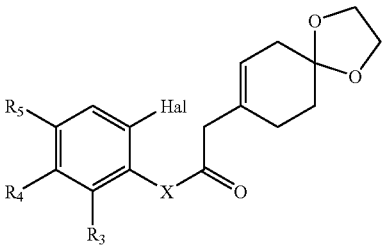

(9)

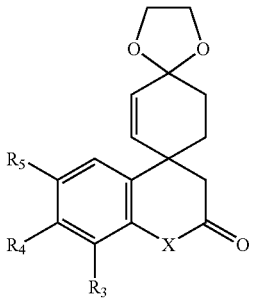

in which Hal, $R_3$, $R_4$, and $R_5$ are as defined above and X represents a sulfur atom, a nitrogen atom, an —SO group, an —$SO_2$ group, a group —$NR_6$ where $R_6$ is as defined above or represents an amine-protective group.

The examples which follow illustrate the invention, though without limiting it.

EXAMPLE 1

Total Synthesis of Galanthamine 1.1 2-iodo-6-methoxyphenyl (1',4'-dioxaspiro[4.5]dec-7'-en-8'-yl)acetate (8)

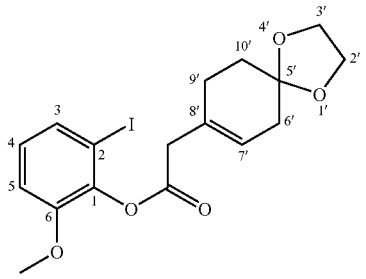

500 mg (2.52 mmol; 1.05 eq) of (1,4-dioxaspiro[4.5]dec-7-en-8-yl)acetic acid (7) in solution in 10 ml of $CH_2Cl_2$ at 0° C. are admixed gradually with 970 mg (5.05 mmol; 2.10 eq) of EDC in solution in 30 ml of $CH_2Cl_2$, then with 308 mg (2.52 mmol; 1.05 eq) of demethylaminopyridine in solution in 10 ml of $CH_2Cl_2$. The reaction mixture is stirred at 0° C. for 15 minutes and then 600 mg (2.4 mmol; 1.00 eq) of 2-iodo-6-methoxyphenol 6 in solution in 10 ml of $CH_2Cl_2$ are added. After 5 hours of stirring at ambient temperature the reaction mixture is hydrolyzed and extracted with ethyl acetate (AcOEt). The organic phase is washed with saturated aqueous sodium chloride solution, dried over magnesium sulfate and evaporated under vacuum. The residue is purified by flash chromatography on silica gel (elution: heptane/AcOEt: 7/3) to give 825 mg (80%) of 2-iodo-6-methoxyphenyl (1',4'-dioxaspiro[4.5]dec-7'-en-8'-yl)acetate 8 in the form of a colorless oil.

Elemental analysis: calculated for $C_{17}H_{19}IO_5$: C, 47.46; H, 4.45; O, 18.59; found: C, 47.34; H, 4.45; O, 18.41.

IR ($CHCl_3$) ν ($cm^{-1}$): 1764 (C═O); 1586 (C═C); 1468 (Car-C); 1267 (Car-O); 1117 (C—O)

MS (EI, m/z): 430 ($M^+$.); 250 ($M^+$.—$C_1OH_{12}O_3$); 180 ($M^+$—$C_7H_7IO_2$)

$^1$H NMR ($CDCl_3$, 200 MHz) δ (ppm): 7.37 (1H, dd, $J_{4-3}$= 6.0, $J_{4-5}$=3.0, H4); 6.95–6.90 (2H, m, H3, H5); 5.67 (1H, broad s, H7'); 4.00 (4H, s, H2', H3'); 3.80 (3H, s, $OCH_3$); 3.32 (2H, s, CH2); 2.47–2.33 (4H, m, H6', H9'); 1.85 (2H, t, J=6.4, H10')

$^{13}$C NMR ($CDCl_3$, 75 MHz) δ (ppm): 168.4 (C═O); 152.2 (C6); 141.7 (C1); 131.3 (C3); 130.1 (C8'); 128.2 (C5); 124.2 (C7'); 112.9 (C6) 107.4 (C5'); 92.4 (C2); 64.8 (C2', C3'); 56.2 (OCH3); 42.3 (CH2); 36.0 (C6'); 31.5 (C10'); 28.4 (C9')

1.2 8-methoxy-3,4,4a,8a-tetrahydro-1',4'-dioxas chromen-2-one-[4,8']-dec-6'-ene (9)

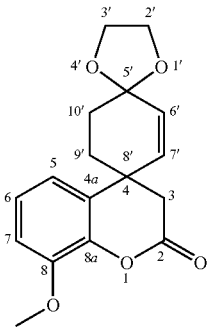

39 mg (0.04 mmol; 0.1 eq) of tris(dibenzylideneacetone) dipalladium and 33 mg (0.08 mmol; 0.2 eq) of 1,2-bis (diphenylphosphino)ethane in solution in 10 ml of MeCN are heated for 30 minutes at 90° C. 117 mg (0.44 mmol; 1.2 eq) of thallium acetate and 160 mg (0.37 mmol; 1.0 eq) of 2-iodo-6-methoxyphenyl (1',4'-dioxaspiro[4.5]dec-7'-en-8'-yl)acetate (8) are then added to the reaction mixture. After 72 hours of stirring at 90° C. the reaction mixture is filtered over Celite and evaporated under reduced pressure.

Purification by chromatography on silica gel (elution: heptane/AcOEt: 7/3) of the residue obtained gives 12.5 mg (67%) of 8-methoxy-3,4,4a,8a-tetrahydro-1',4'-dioxaspiro-chromen-2-one-[4,8']-dec-6'-ene 9, isolated in the form of a white powder.

m.p.: 101° C.

Elemental analysis: calculated for $C_{17}H_{18}O_5$: C, 67.54; H, 6.00; O, 26.46; found: C, 67.37; H, 6.05; O, 26.46.

HRMS (CI, m/z): calculated for $C_{17}H_{19}O_5^+$: 303.11543; found: 303.12277.

IR ($CHCl_3$) ν ($cm^{-1}$): 1766 (C═O); 1583 (C═C); 1481 (CAR-C); 1233 (Car-O); 1090 (C—O)

MS (CI, m/z): 303 ($MH^+$)

$^1$H NMR ($CDCl_3$, 200 MHz) δ (ppm): 7.08 (1H, dd, $J_{6-5}$=$J_{6-7}$=8.0, H6); 6.91 (1H, dd, $J_{7-6}$=8.0, $J_{7-5}$=1.5, H7); 6.81 (1H, dd, $J_{5-6}$=8.0, $J_{5-7}$=1.5, H5); 5.94 (1H, d, $J_{6-7}$=10.0, H6'); 5.68 (1H, d, J7'-6'=10.0, H7'); 4.05–3.97 (4H, m, H2', H3'); 3.90 (3H, s, $OCH_3$); 2.80 (1H, d, $J_{gem}$=15.4, H3); 5.38 (1H, d, $J_{gem}$=15.4, H3); 1.95–1.76 (4H, m, H9', H10')

$^{13}$C NMR ($CDCl_3$, 50 MHz) δ (ppm): 166.7 (C2); 148.6 (C8); 140.1 (C8a); 134.8 (C6'); 131.4 (C7'); 128.6 (C4a); 124.1 (C5); 119.9 (C6) 112.4 (C7); 105.8 (C5'); 65.9 (C2', C3'); 60.1 (OCH3); 41.5 (C3); 39.0 (C4); 32.8 (C10'); 30.4 (C9')

1.3 8-methoxy-3,4,4a,8a-tetrahydrospirochromen-2-one-[4,4']-cyclohex-2'-en-1'-one (10)

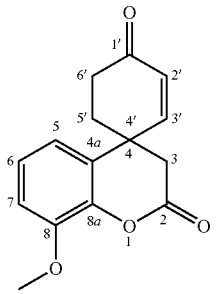

1.10 g (3.68 mmol; 1.0 eq) of 8-methoxy-3,4,4a,8a-tetrahydro-1',4'-dioxaspirochromen-2-one-[4,8']-dec-6'-ene (9) dissolved in 50 ml of anhydrous $CH_2Cl_2$ are admixed with 1.21 g (3.68 mmol; 1.0 eq) of triphenyl-carbenium tetrafluoroborate. After 1 hour of stirring at ambient temperature the reaction mixture is hydrolyzed with water and then extracted with $CH_2Cl_2$. The organic phase is washed with saturated aqueous sodium choride solution, dried over magnesium sulfate and evaporated under vacuum. Purification by flash chromatography on silica gel (elution: heptane/AcOEt: 8/2 then 5/5) of the residue obtained gives 940 mg (100%) of 8-methoxy-3,4,4a,8a-tetrahydrospirochromen-2-one-[4,4']-cyclohex-2'-en-1'-one (10), isolated in the form of a white powder.

m.p.: 130° C.

Elemental analysis: calculated for $C_{15}H_{14}O_4$: C, 69.76; H, 5.46; O, 24.78; found: C, 69.53; H, 5.61; O, 24.76.

IR($CHCl_3$) ν ($cm^{-1}$): 1770 (C═O); 1680 (O—C═O); 1585 (Car-C); 1480 (Car-C); 1248 (Car-O)

MS (CI, m/z): 259 ($MH^+$)

$^1$H NMR ($CDCl_3$, 300 MHz) δ (ppm): 7.13 (1H, dd, $J_{6-5}$=$J_{6-7}$=8.0, H6); 6.98 (1H, dd, $J_{7-6}$=8.0, $J_{7-5}$=1.3, H7); 6.75 (1H, dd, $J_{5-6}$=8.0, $J_{5-7}$=1.3, H5); 6.70 (1H, d, $J_{3'-2'}$=10.1, H3'); 6.30 (1H, d, J2'-3'=10.1, H2'); 3.92 (3H, s, OCH3); 2.93 (1H, d, $J_{gem}$=15.5, H3); 2.86 (1H, d, $J_{gem}$=15.5, H3); 2.44 (2H, dd, J5'-6'=6.0, $J_{gem}$=12, H5'); 2.19 (2H, dd, J6'-5'=6.0, H6')

$^{13}$C NMR ($CDCl_3$, 75 MHz) δ (ppm): 198.7 (C1'); 165.4 (C2); 150.1 (C3'); 148.9 (C8); 140.0 (C8a); 132.5 (C2'); 127.5 (C4a); 125.1 (C5) 118.3 (C6); 112.7 (C7); 56.3 (OCH3); 40.4 (C3); 39.2 (C4); 34.7 (C6'); 33.5 (C5')

1.4 8-methoxy-3,4,4a,8a-tetrahydro-spiro-chromen-2-one-[4,4']-cyclohex-2',5'-dien-1'-one (11)

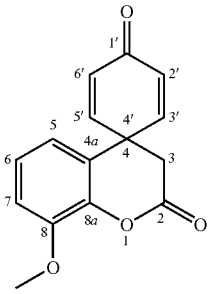

125 mg (0.48 mmol; 1.0 eq) of 8-methoxy-3,4,4a,8a-tetrahydro-spiro-chromen-2-one-[4,4']-cyclohex-2'-en-1'-one (10) in solution in 12 ml of anhydrous chlorobenzene containing 400 mg of silica and 400 mg of alumina are admixed with 691 mg (1.92 mmol; 4.0 eq) of benzeneselinic anhydride. After 24 hours of stirring at reflux the reaction mixture is filtered on a frit, rinsed with MeOH and evaporated under reduced pressure. The residue is taken up in $CH_2Cl_2$ and then washed with saturated aqueous sodium chloride solution. The organic phase is dried over magnesium sulfate and evaporated under vacuum. Purification by flash chromatography on silica gel (elution: heptane then heptane/AcOEt: 5/5) of the residue obtained gives 62 mg (50%) of 8-methoxy-3,4,4a,8a-tetrahydro-spiro-chromen-2-one-[4,4']-cyclo-hex-2',5'-dien-1'-one (11), isolated in the form of a yellow powder.

m.p.: 176–178° C.

HRMS (CI, m/z): calculated for $C_{15}H_{13}O_4^+$: 257.08139; found 257.08132.

IR ($CHCl_3$) ν ($cm^{-1}$): 1776 (C═O ketone); 1671 (C═O lactone); 1631 (C═C); 1281 (Car-O); 1179 (C—O)

MS (CI, m/z): 257 ($MH^+$); 238 ($MH^+$-$H_2O$): 229 ($MH^+$—CO)

$^1$H NMR ($CDCl_3$, 300 MHz) δ (ppm): 7.08 (1H, dd, $J_{6-5}$=$J_{6-7}$=8.1, H6); 6.96 (1H, d, $J_{7-6}$=8.1, H7); 6.89 (2H, d, $J_{3'-2'}$=$J_{5'-6'}$=10.3, H3', H5'); 6.54 (1H, d, $J_{5-6}$=8.1, H5); 6.39 (2H, d, $J_{2'-3'}$=$J_{6'-5'}$=10.3, H2', H6'); 3.90 (3H, s, $OCH_3$); 2.90 (2H, s, H3)

$^{13}$C NMR ($CDCl_3$, 75 MHz) δ (ppm): 184.5 (C1'); 164.6 (C2); 148.4 (C8); 148.1 (C3', C5'); 140.8 (C8a); 130.0 (C2', (C6'); 125.4 (C6); 123.1 (C4a); 117.6 (C5); 113.0 (C7); 56.3 ($OCH_3$); 42.8 (C4); 38.5 (C3)

1.5 4a,9b-Dihydro-6-methoxy-9b-{[N-methylamino)-carbonyl]methyl}-dibenzofuran-3-one (12)

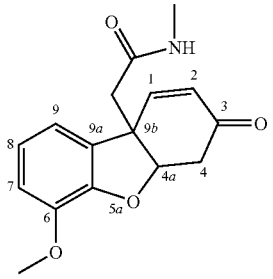

122 mg (0.43 mmol; 1.0 eq) of 8-methoxy-3,4,4a,8a-tetrahydro-spiro-chromen-2-one-[4,4']-cyclohex-2',5'-dien-1'-one (11) in solution in 15 ml of tetrahydrofuran are admixed with 0.13 ml (1.51 mmol; 3.5 eq) of methylamine in solution (40%) in water. After 20 minutes of stirring at ambient temperature the reaction mixture is washed with saturated aqueous sodium chloride solution and extracted with $CH_2Cl_2$. The organic phase is washed with saturated aqueous sodium chloride solution, dried over magnesium sulfate and evaporated under vacuum. Purification by flash chromatography on silica gel (elution: $CH_2Cl_2$/MeOH: 95/5) of the residue obtained gives 137 mg (100%) of 4a,9b-dihydro-6-methoxy-9b-{[N-methylamino)carbonyl] methyl}dibenzofuran-3-one (12), isolated in the form of a yellow paste.

HRMS (CI, m/z): calculated for $C_{16}H_{18}NO_4^+$: 288.12359; found: 288.12350.

IR ($CHCl_3$) ν (cm-'): 3461 (N—H); 1680 (C═O ketone) (C═O amide); 1620 (C═C); 1282 (Car-O)

MS (EI, m/z): 287 ($M^+$.); 214 ($M^+$.—$C_3H_6NO$)

$^1$H NMR ($CDCl_3$, 300 MHz) δ (ppm): 6.87 (3H, m, H7, H8, H9); 6.61 (1H, dd, $J_{1-4a}$=1.8, $J_{1-2}$=10.0, H1); 6.05 (1H, broad s, NH); 5.98 (1H, d, $J_{2-1}$=10.0, H2); 5.14 (1H, broad s, H4a); 3.85 (3H, s, $OCH_3$); 3.16 (1H, dd, $J_{4-4a}$=4.5, $J_{gem}$=17.5, H4); 3.06 (1H, dd, J4-4a=2.5, $J_{gem}$=17.5, H4); 2.91 (2H, d, $J_{gem}$=15.0, $CH_2$); 2.78 (3H, s, $NCH_3$); 2.76 (3H, s, $NCH_3$)

$^{13}$C NMR ($CDCl_3$, 75 MHz) δ (ppm): 195.8 (C3); 169.4 (C═O); 147.3 (C1); 146.8 (C6); 145.0 (C9a); 131.8 (C5a); 127.0 (C2); 122.4 (Car); 115.0 (Car); 112.5 (Car); 86.2 (C4a); 56.0 (OCH3); 47.7 (C9b); 43.4 (CH2); 38.7 (C4); 26.4 ($NCH_3$)

1.6 (±)-11-oxonarwedine or (±)-6-methoxy-10-methyl-galantham-1-ene-3,11-dione (1a)

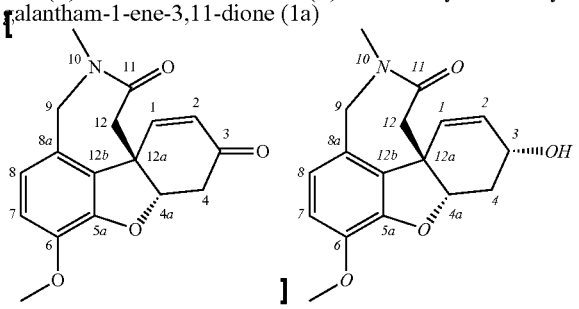

90 mg (0.31 mmol; 1.0 eq) of 4a,9b-dihydro-6-methoxy-9b-{[N-methylamino)carbonyl]methyl}-dibenzofuran-3-one (12) in solution in 10 ml of 1,2-dichloroethane are admixed with 38 mg (1.26 mmol; 4.0 eq) of paraformaldehyde and 0.3 ml (3.93 mmol; 12.5 eq) of trifluoroacetic acid. After 20 hours of stirring at 60° C. the reaction mixture is washed with saturated aqueous sodium hydrogencarbonate solution and extracted with $CH_2Cl_2$. The organic phase is washed with saturated aqueous sodium chloride solution, dried over magnesium sulfate and evaporated under vacuum. Purification by flash chromatography on silica gel (elution: $CH_2Cl_2$/MeOH: 95/5) of the residue obtained gives 59 mg (63%) of (±)-11-oxo-narwedine (13), isolated in the form of a colorless paste.

HRMS (CI, m/z): calculated for $C_{17}H_{17}NO_4^+$: 300.12359; found: 300.12366.

IR ($CHC_{13}$) ν ($cm^{-1}$): 1723 (C═O ketone); 1680 (C═O amide); 1641 (C═C); 1509 (Car-C); 1285 (Car-O)

MS (CI, m/z): 300 ($MH^+$)

$^1$H NMR ($CDCl_3$, 300 MHz) δ (ppm): 6.75 (2H, s, H7, H8); 6.39 (1H, dd, $J_{2-4a}$=2.7, $J_{1-2}$=10.2, H1); 6.06 (1H, d, $J_{2-1}$=10.2, H2); 4.85 (1H, d, $J_{4a-4}$=2.7, H4a); 4.51 (1H, d, $J_{gem}$=16.2, H9); 4.41 (1H, d, $J_{gem}$=16.2, H9); 3.86 (3H, s, $OCH_3$); 3.17 (1H, dd, $J_{4-4a}$=2.7, $J_{gem}$=17.7, H4); 3.06 (3H, s, $NCH_3$); 3.03 (1H, d, $J_{gem}$=13.8, H12); 2.96 (1H, d, $J_{gem}$=13.8, H12); 2.83 (1H, dd, $J_{4-4a}$=2.7, $J_{gem}$=17.7, H4)

$^{13}$C NMR ($CDCl_3$, 75 MHz) δ (ppm): 193.7 (C3); 170.1 (C11); 147.6 (C6); 144.8 (C1, C5a); 129.8 (C12b); 127.7 (C2); 124.9 (C8a); 120.3 (Car); 112.7 (Car); 87.1 (C4a); 56.3 ($OCH_3$); 51.9 (C9); 43.8 (C12a); 40.5 (C12); 36.4 (C4); 36.0 ($NCH_3$)

1.7 (±)-11-oxo-galanthamine or (±)-6-methoxy-10-methyl-galantham-1-en-3α-ol-11-one (1b)

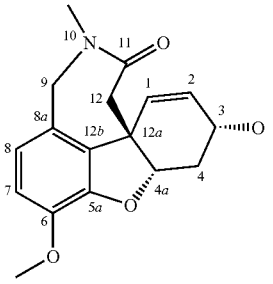

20 mg (0.07 mmol; 1.0 eq) of (±)-11-oxo-narwedine 13 in solution in 2 ml of THF are admixed with 0.10 ml (0.10 mmol; 1.5 eq) of L-Selectride® in solution (1M) in THF. After 1 hour of stirring at −78° C. the reaction mixture is quenched with methanol and then evaporated under reduced pressure. The residue is taken up in AcOEt and washed with saturated aqueous sodium carbonate. solution. The organic phase is washed with saturated aqueous sodium chloride solution, dried over magnesium sulfate and evaporated under vacuum. Purification by preparative plate (elution: $CH_2Cl_2$/MeOH: 95/5) of the residue obtained gives 18.5 mg (93%) of (±)-10-oxogalanthamine (14), isolated in the form of a white powder.

m.p.: 191–192° C.

HRMS (CI, m/a): calculated for $C_{17}H_{20}NO_4^+$: 302.13924; found: 302.13923.

IR. ($CHCl_3$) ν ($cm^{-1}$): 3557 (O—H); 1641 (C═O) (C═C); 1509 (Car-C); 1284 (Car-O)

MS (CI, m/z): 302 ($MH^+$); 284 ($M^+$-OH); 258 ($M^+$-$C_2H_5N$)

$^1$H NMR ($CDCl_3$, 300 MHz) δ (ppm): 6.72 (2H, s, H7, H8); 6.04 (1H, dd, $J_{2-3}$=5.4, $J_{2-1}$=10.2, H2); 5.51 (1H, d, $J_{1-2}$=10.2, H1); 4.76 (1H, broad t, $J_{4a-4}$=1.8, H4a); 4.46 (1H, d, $J_{gem}$=15.9, H9); 4.34 (1H, d, $J_{gem}$=15.9, H9); 4.17 (1H, broad t, $J_{3-2}$=5.4, H3); 3.87 (3H, s, $OCH_3$); 3.04 (3H, s, $NCH_3$); 2.81 (1H, d, $J_{gem}$=14.1, H12) 2.74 (1H, d, $J_{gem}$=14.1, H12); 2.68 (1H, dd, $J_{4-3}$=3.6, $J_{gem}$=15.9, H4); 2.40 (1H, broad s, OH); 2.11 (1H, ddd, $J_{4-4a}$=1

$^{13}$C NMR ($CDCl_3$, 75 MHz) δ (ppm): 171.0 (C11); 146.7 (C6); 144.9 (C5a); 132.2 (C12b); 128.4 (C1, C2); 125.2 (C8a); 120.2 (Car); 112.1 (Car); 112.1 (Car); 88.4 (C4a); 61.6 (C3); 56.2 ($OCH_3$); 52.1 (C9); 43.4 (C12a); 41.6 (C12); 36.0 ($NCH_3$); 29.3 (C4)

1.8 (±)-galanthamine (1c)

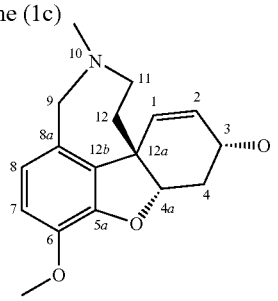

6 mg (0.15 mmol; 5.5 eq) of lithium aluminum hydride in suspension in 5 ml of DME are admixed dropwise at 0° C. with 9 mg (0.06 mmol; 1.0 eq) of (±)-11-oxogalanthamine (1c) dissolved in 5 ml of DME. After 12 hours of stirring at 50° C. the reaction mixture is quenched with 10% sodium dithionite solution and then filtered over Celite (chloroform elution). The filtrate obtained is washed with 10% aqueous sodium dithionite solution and extracted with chloroform. The organic phase is washed with saturated aqueous sodium chloride solution, dried over magnesium sulfate and evaporated under vacuum. Purification by preparative plate (elution: $CH_2Cl_2$/MeOH: 90/10) of the residue obtained gives 7 mg (80%) of (±)-galanthamine (1c), isolated in the form of a white, powder.

IR (CHCl3) ν ($cm^{-1}$): 3562 (O—H); 1626 (C═C); 1599 (Car-C); 1508 (Car-C); 1280 (Car-O)

MS (CI, m/z): 287 ($M^+$.); 270 ($M^+$.-OH); 244 ($M^+$.-$C_2H_5N$); 230 ($M^+$.-$C_3$H7N); 216 ($M^+$.-$C_4H_9N$)

$^1$H NMR ($CDCl_3$, 250 MHz) 6 (ppm): 6.67 (1H, d, $J_{1-2}$=8.3, Har); 6.63 (1H, d, $J_{1-2}$=8.3, Har); 6.07 (1H, dd, $J_{1-3}$=1.0, $J_{1-2}$=10.3, H1); 6.01 (1H, dd, $J_{2-3}$=4.3, $J_{2-1}$=10.3, H2); 4.62 (1H, broad s, H4a); 4.14 (1H, broad t, J=5.0, H3); 4.11 (1H, d, $J_{gem}$=15.3, H9); 3.84 (3H, S, $OCH_3$); 3.70 (1H, d, $J_{gem}$=15.3, H9); 3.30 (1H, td, $J_{11-12}$=1.5, $J_{gem}$=14.3, H11); 3.07 (1H, dt, $J_{11-12}$=3.5, $J_{gem}$=14.3, H11); 2.69 (1H, dt, $J_{4-4a}$=2.0, $J_{gem}$=15.8, H4); 2.48 (1H, broad s, OH); 2.41 (3H, s, $NCH_3$); 2.12 (1H, dd, $J_{12-11}$=3.5, $J_{gem}$=13.5, H12); 2.01 (1H, ddd, $J_{4-4a}$=2.0, $J_{4-3}$=5.0, $J_{gem}$=15.8, H4); 1.59 (1H, ddd, $J_{12-11}$=1.5, $J_{12-11}$=3.5, $J_{gem}$=13.5, H9)

$^{13}$C NMR ($CDCl_3$, 75 MHz) δ (ppm): 146.0 (C6); 144.3 (C5a); 133.2 (C12b); 129.2 (C8a); 127.8 (C1); 127.0 (C2); 122.3 (C8); 111.4 (C7); 88.9 (C4a); 62.2 (C3); 60.6 (C9); 56.1 ($OCH_3$); 53.9 (C11) 48.3 (C12a); 42.0 (NCH3); 33.8 (C12); 30.1 (C4)

EXAMPLE 2

Total Synthesis of Azagalanthamine 2.1 2-(1,4-dioxaspiro[4.5]dec-7-en-8-yl)-N-(2'-iodo-6'-methoxyphenyl)acetamide (16)

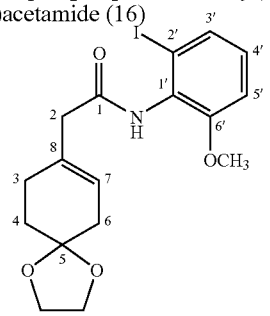

A solution of (1,4-dioxaspiro[4.5]dec-7-en-8-yl) acetic acid (567 mg; 2.86 mmol; 1 eq) (7) and 2-iodo-6-methoxyaniline (1 g; 2.86 mmol; 1 eq) in anhydrous dichloromethane (30 mL) is admixed with 2-chloro-1-methylpyridinium iodide (1.46 g; 5.73 mmol; 2 eq) and triethylamine (3.98 mL; 28.65 mmol; 10 eq). The reaction mixture is heated at reflux for 20 hours. After cooling and acidification with 1N HCl solution to pH=5–6, the mixture is extracted with dichloromethane. The organic phases are washed with saturated aqueous sodium chloride solution, dried over magnesium sulfate and evaporated under vacuum. Purification by flash chromatography on silica gel (eluent: heptane/ethyl acetate 4/6) gives 1.10 g of 2-(1,4-dioxaspiro[4.5]dec-7-en-8-yl)-N-(2'-iodo-6'-methoxy-phenyl) acetamide (16) in the form of a yellow foam (yield: 90%).

Elemental analysis calculated for $C_{17}H_{20}INO_4$ (m.p.: 429.25) C: 47.57; H: 4.70; N: 3.26; O: 14.91; found C: 47.39; H: 4.59; N: 3.01; O: 15.16.

IR ($CHCl_3$) ν ($cm^{-1}$): 3382 (N—H); 1687 (C═O)

MS (ES) m/z: 429.8 [$M^+$H]$^+$.

$^1$H NMR ($CDCl_3$; 300 MHz) δ (ppm): 7.43 (dd, J=8.0, J=1.2; 1H; H3'); 7.18 (broad s; 1H; NH); 6.98 (t, J=8.0; 1H; H4'); 6.91 (dd, J=8.0, J=1.2; 1H; H5'); 5.72 (broad s, 1H; H4); 3.99 (s; 4H; Hdioxolane); 3.80 (s; 3H; $OCH_3$); 3.15 (s; 2H; H2); 2.45 (broad s; 1H; H8); 2.37 (broad s, 1H; H5); 2.37 (broad s, 2H; H6); 1.85 (t, J=6.4; 2H; H7).

$^{13}$C NMR ($CDCl_3$; 62.9 MHz) δ (ppm): 169.2 (C(O)NH); 155.5 (C6'); 132.9 (C1'); 130.8 (C3'); 129.6 (C4'); 128.1 (C8); 124.9 (C7); 111.7 (C5'); 107.7 (C5); 99.8 (C2'); 64.8 (Cdioxolane); 56.1 ($OCH_3$); 45.7 (C2); 35.9 (C6); 38.2 (C4); 35.0 (C3).

2.2 2-(1,4-dioxaspiro[4.5]dec-7-en-8-yl)-N-(2'-iodo-6'-methoxyphenyl)-N-methylacetamide (17)

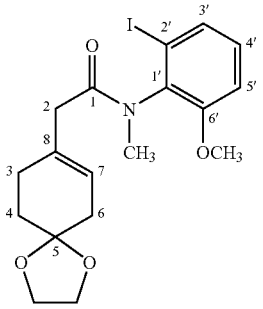

A solution of 2-(1,4-dioxaspiro[4.5]dec-7-en-8-yl)-N-(2'-iodo-6'-methoxyphenyl)acetamide (16) (1.88 g; 4.39 mmol; 1 eq) in 150 mL of anhydrous tetrahydrofuran (THF) is admixed dropwise at 0° C. with a suspension of NaH (263 mg; 10.98 mmol; 2.5 eq) in anhydrous THF (120 mL). After 15 minutes the reaction mixture is allowed to return to ambient temperature and dimethyl sulfate (1.04 mL; 0.2 mmol; 2.5 eq) is added. The reaction mixture is kept with stirring at ambient temperature for 2 hours and then the reaction is stopped by adding saturated aqueous sodium hydrogencarbonate solution. Following extraction with ether, the organic phases are washed with saturated aqueous sodium chloride solution, dried over magnesium sulfate and evaporated under vacuum. Purification by flash chromatography on silica gel (eluent: heptane/ethyl acetate 4/6) of the residue obtained allows 26.9 mg of the product 2-(1,4-dioxaspiro-[4.5]dec-7-en-8-yl)-N-(2'-iodo-6'-methoxyphenyl)-N-methylacetamide (17) to be obtained in the form of a colorless oil (yield: 86%). The 1H NMR spectrum reveals that the product is a mixture of two rotamers in approximately 1:4 proportion.

Elemental analysis calculated for $C_{18}H_{22}INO_4$ (m.p.: 443.28) C: 48.77; H: 5.00; found: C 48.98; H: 4.88.

IR ($CHCl_3$) ν ($cm^{-1}$): 1652 (C═O); 1602 (C═C).

MS (ES) m/z: 443.9 [$M^+$H]$^+$.

$^1$H NMR ($CDCl_3$; 300 MHz) δ (ppm) for the majority rotamer: 7.44 (dd, J=8.0, J=1.3; 1H; H3'); 7.01 (t, J=8.0; 1H;

H4'); 6.90 (dd, J=8.0, J=1.3; 1H; H5'); 5.06 (broad s; 1H; H7); 3.94 (s; 4H; Hdioxolane); 3.81 (s; 3H; $OCH_3$); 3.08 (s; 3H; NCH3); 2.73–2.65 (AB system, Jab=15.0; 2H; H2a and H2b); 2.21 (broad s; 2H; H3); 2.19 (broad s; 2H; H6); 1.78 (m; 2H; H4).

$^{13}C$ NMR ($CDCl_3$; 75.4 MHz) δ (ppm) for the majority rotamer: 171.3 (C(O)NMe); 156.3 (C6'); 134.8 (C1'); 131.1 (C8); 131.0 (C3'); 130.7 (C4'); 122.5 (C7); 111.7 (C5'); 107.9 (C5); 101.7 (C2'); 64.3 (Cdioxolane); 55.9 (OCH3); 42.2 (C2); 35.8 (C6); 34.5 ($NCH_3$); 31.0 (C4); 27.5 (C3).

2.3 8-methoxy-1-methyl-3,9',10'-dihydro-1H-1',4'-dioxaspiroquinolin-2-one-[4,8']-dec-6'-ene (18)

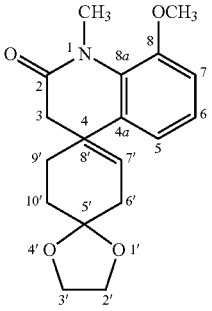

A solution of tris(dibenzylideneacetone)dipalladium (36.8 mg; 0.04 mmol; 0.05 eq) and 1,2-bis (diphenylphosphino)ethane (32.1 mg; 0.08 mmol; 0.1 eq) in anhydrous dimethylacetamide (10 mL) is kept with stirring at ambient temperature for 15 minutes. A solution of 2-(1,4-dioxaspiro[4.5]dec-7-en-8-yl)-N-(2'-iodo-6'-methoxyphenyl)-N-methylacetamide (17) (357 mg; 0.81 mmol; 1 eq) and 1,2,2,6,6-pentamethylpiperidine (582 μL; 3.22 mmol; 4 eq) in anhydrous dimethylacetamide (30 mL) is then added dropwise and the reaction mixture is heated at 110° C. for 23 hours. After cooling to ambient temperature, addition of saturated aqueous sodium hydrogencarbonate solution, and extraction with ethyl acetate, the organic phases are washed with saturated aqueous sodium chloride solution, dried over magnesium sulfate and evaporated under vacuum. After purification by flash chromatography on silica gel (eluent: heptane/ethyl acetate 4/6) 15.0 mg of the product 8-methoxy-1-methyl-3,9',10'-dihydro-1H-1',4'-dioxaspiroquinolin-2-one-[4,8']-dec-6'-ene (18) are obtained in the form of a pale yellow oil (yield: 80%).

HRMS (CI, m/z); calculated for $C_{18}H_{21}NO_4^+$: 315.15; found: 315.14794.

IR ($CHC_{13}$) ν ($cm^{-1}$): 1659 (C═O lactam).

MS (ES) m/z: 316.2 $[M^+H]^+$; 338.2 $[M^+Na]^+$ $^1H$ NMR ($CDCl_3$; 300 MHz) δ (ppm): 7.04 (t, J=8.0; 1H; H6); 6.88 (dd, J=8.0, J=1.3; 1H; H5); 6.82 (dd, J=8.0, J=1.3; 1H; H7); 5.88 (d, J=10.0; 1H; H6'); 5.62 (d, J=10.0; 1H; H7'); 4.03–3.90 (m; 4H; Hdioxolane); 3.85 (s; 3H; OCH3); 3.39 (s; 3H; $NCH_3$); 2.58–2.48 (AB system, Jab=15.0; 2H; H3a and H3b); 1.85–1.73 (m; 4H; H9' and H10').

$^{13}C$ NMR ($CDCl_3$; 75.4 MHz) δ (ppm): 170.1 (C(O) NMe); 150.4 (C8); 136.2 (C7'); 135.0 (C8a); 130.5 (C6'); 130.2 (C4a); 124.8 (C6); 119.4 (C5); 112.4 (C7); 105.3 (C5'); 64.8 and 64.6 (Cdioxolane); 56.2 ($OCH_3$); 44.0 (C3); 39.2 (C4); 34.7 ($NCH_3$); 30.4 and 30.0 (C9' and C10').

2.4 8-methoxy-1-methyl-3,4-dihydro-1H-quinolin-2-one-[4.4']-cyclohex-5'-ene-1'-one (19)

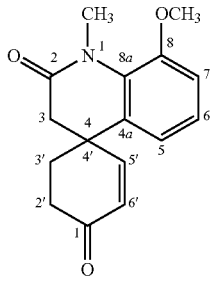

1.10 g (3.49 mmol; 1.0 eq) of 8-methoxy-1-methyl-3,9',10'-dihydro-1H-1',4'-dioxaspiroquinolin-2-one-[4,8']-dec-6'-ene (18) dissolved in 60 ml of anhydrous $CH_2Cl_1$ are admixed with 1.15 g (3.49 mmol; 1.0 eq) of triphenylcarbenium tetrafluoroborate. After 1 hour of stirring at ambient temperature the reaction mixture is hydrolyzed with water and then extracted with $CH_2Cl_2$. The organic phase is washed with saturated aqueous sodium chloride solution, dried over magnesium sulfate and evaporated under vacuum. Purification by flash chromatography on silica gel (elution: heptane/AcOEt: 4/6) of the residue obtained gives 898.5 mg of 8-methoxy-1-methyl-3,4-dihydro-1H-quinolin-2-one-[4.4']-cyclohex-5'-en-1'-one (19), isolated in the form of a yellow foam (yield: 95%).

HRMS (CI, m/z): calculated for $C_{16}H_{17}NO_3^+$: 271.12; found: 271.12114.

IR ($CHCl_3$) ν ($cm^{-1}$): 3000 (C—H); 1677 (C═O amide; C═O enone); 1370 (C═C); 1262 (C—OMe); 1086 (C—H.Ar).

MS (EI) m/z: 271 $[M^+.]$.

$^1H$ NMR ($CDCl_3$; 250 MHz) δ (ppm): 7.08 (q; J=8.4; J=7.6; 1H; H6); 6.96 (q; J=8.4; J=1.4; 1H; H5); 6.77(q; J=7.6; J=1.4; 1H; H7); 6.63 (d; J=10.2; 1H; H5'); 3.88 (s; 3H; OCH3); 3.42 (s; 3H; NCH3); 2.68 (system AB; 2H, H3a and H3b; Jab=15.1); 2.43 (m; 2H; H3'); 2.10 (t; J=6.9; 2H; H2').

$^{13}C$ NMR ($CDCl_3$; 75.4 MHz) δ (ppm): 198.8 (C1'); 169.0 (C2); 152.4 (C5'); 150.6 (C8); 132.6 (C8a); 131.1 (C6'); 130.1 (C4a); 125.1 (C6); 118.5 (C7); 112.8 (C5); 56.1 ($OCH_3$); 43.0 (C3); 39.8 (C4); 34.7 ($NCH_3$); 33.8 (C2'); 31.5 (C3').

2.5 8-methoxy-1-methyl-3,4-dihydro-1H-quinolin-2-one-[4.4']-cyclohex-2',5'-dien-1'-one (20)

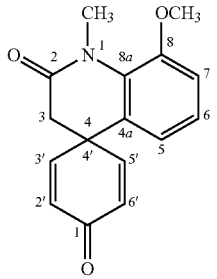

120 mg (0.44 mmol; 1.0 eq) of 8-methoxy-1-methyl-3,4-dihydro-1H-quinolin-2-one-[4.4']-cyclohex-5'-ene-1'-one 19 in solution in 10 ml of chlorobenzene containing 400 mg of alumina and 400 mg of silica are admixed with 637 mg (1.77 mmol; 4.0 eq) of benzeneselinic anhydride. After 24 hours of stirring at reflux the reaction mixture is filtered on a frit, washed with MeOH and evaporated under reduced pressure.

The residue is taken up in and extracted with $CH_2Cl_2$, the aqueous phase being saturated with sodium chloride. The organic phase is washed with saturated aqueous sodium chloride solution, dried over magnesium sulfate and evaporated under vacuum. Purification by flash chromatography on silica gel (elution: heptane/ethyl acetate: 3.5/6.5) of the residue obtained gives 73 mg of 8-methoxy-1-methyl-3,4-dihydro-1H-quinolin-2-one-[4.4']-cyclohex-2',5'-dien-1'-one (20), isolated in the form of a yellow foam (yield: 61%).

Elemental analysis calculated for C16H15NO3 (m.p.: 269) C: 71.36; H: 5.61; N: 5.20; O: 17.82; found: C: 69.33; H: 5.58; N: 5.19; O: 17.38.

IR ($CHCl_3$) ν ($cm^{-1}$): 2962 (C—H); 1669 ($C{=}O_{amide}$; $C{=}O_{dienone}$); 1600 (C=C); 1370 (C—N); 1261 ($C—OCH_3$); 1097 (C—H.Ar).

MS (EI) m/z: 269 [$M^+$.].

$^1$H NMR ($CDCl_3$; 300 MHz) δ (ppm): 7.06 (q; J=7.9; J=8.1; 1H; H6); 6.95 (q; J=8.3; J=1.3; 1H; H7); 6.89 (d; J=9.8; 2H; H3' and H5'); 6.65 (q; J=1.0; J=7.6; 1H; H5); 6.37 (d; J=9.8; 2H; H2' and H6'); 3.88 (s; 3H; $OCH_3$); 3.47 (s; 3H; $NCH_3$); 2.70 (s; 2H; H3).

$^{13}$C NMR ($CDCl_3$; 75.4 MHz) δ (ppm): 185.0 (C1'); 168.2 (C2'); 150.4 (C8); 149.0 (C3'/C5'); 130.4 (C4a); 129.8 (C2'/C6'); 129.3 (C8a); 125.5 (C6); 118.2 (C5); 113.3 (C7); 56.0 ($OCH_3$); 43.5 (C3); 34.7 ($NCH_3$).

2.6 (±)-11-oxoazanarwedine(21)

This compound is prepared from 8-methoxy-1-methyl-3,4-dihydro-1H-quinolin-2-one-[4.4']-cyclohex-2',5'-dien-1'-one (20) in accordance with the procedure described in steps 1.5 and 1.6 of example 1.

2.7 (±)azagalanthamine (22)

This compound is obtained from (21) in accordance with the procedure described in steps 1.7 and 1.8 of example 1.

The invention claimed is:

1. A method of synthesizing compounds of formula (1)

(1)

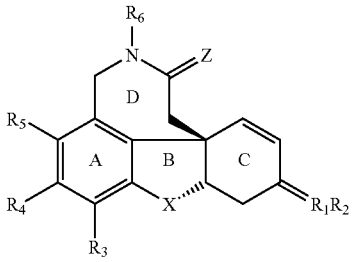

in which either $R_1$ represents a hydrogen atom and $R_2$ represents a hydroxyl group, or $R_1$ and $R_2$ together form=O, $R_3$, $R_4$ and $R_5$ represent each independently of one another a hydrogen atom, a hydroxyl group or a ($C_1$–$C_{12}$)alkoxy group, $R_6$ represents a hydrogen atom, a ($C_1$–$C_{12}$)alkyl group, a group —$(CH_2)_nNR_7R_8$ or a group —$(CH_2)_nN^+R_7R_8R_9$ where n=1 to 12, $R_7$ and $R_8$ represent each independently of one another a hydrogen atom; a cyano; ($C_1$–$C_4$)alkyl; aryl($C_1$–$C_4$)alkyl; aryl($C_1$–$C_4$)alkenyl; ($C_1$–$C_4$)alkyl-carbonyl or arylcarbonyl radical; the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals; and $R_9$ represents a hydrogen atom or a cyano, ($C_1$–$C_4$)alkyl, aryl($C_1$–$C_4$)alkyl, aryl ($C_1$–$C_4$)alkenyl, alkylcarbonyl or arylcarbonyl radical, the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals;

Z represents either two hydrogen atoms or one oxygen atom, and

X represents alternatively an oxygen atom or a sulfur atom on an —SO group or an —$SO_2$ group or a group —$NR_6$ where $R_6$ is as defined above or represents an amine-protective group, comprising providing an α,β-ethylenic ketone of formula (10)

(10)

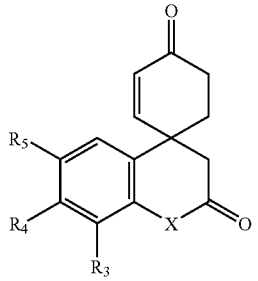

and oxidizing said ketone to a spirodienone of formula (11)

(11)

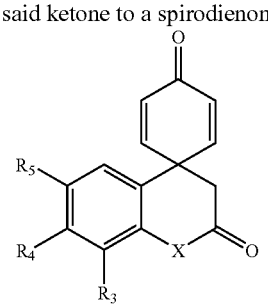

wherein said spirodienone of formula (11) is thereafter transformed to produce a compound of formula (1).

2. A method according to claim 1, characterized in that the oxidation is performed in the presence of benzeneselininic anhydride and a support.

3. A method according to claim 2, characterized in that the support is selected from the group consisting of molecular sieves and mixtures of silica and alumina.

4. A method according to claim 3, characterized in that the mixture of silica and alumina is a 50/50 mixture.

5. A method according to claim 1, characterized in that a compound of formula (6)

(6)

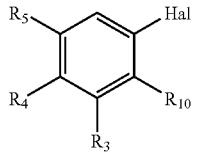

in which Hal represents a halogen atom selected from bromine and iodine atoms, $R_3$, $R_4$, and $R_5$ are as defined in claim 1, and $R_{10}$ represents an amine group or a hydroxyl group is reacted with (1,4-dioxaspiro[4.5]dec-7-en-8-yl) acetic acid of formula (7), (7)

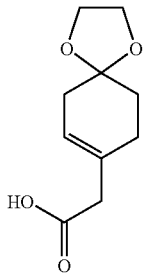

and a compound of formula (8)

(8)

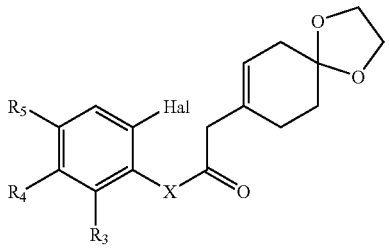

is obtained which is cyclized by an intramolecular Heck reaction to give a compound of formula (9)

(9)

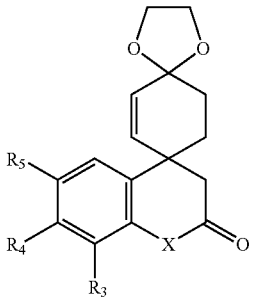

in the presence of a palladium or a palladium(0) precursor catalyst and of bidentate alkylphosphine ligands in a solvent, then the dixolane function of the compound of formula (9) is deprotected to give the α,β-ethylenic ketone of formula (10)

(10)

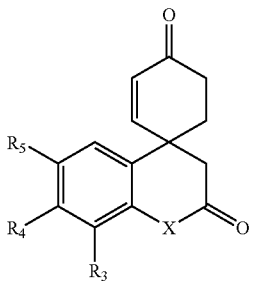

which is oxidized in the presence of benzeneseleninic anhydride, to which a mixture of silica and alumina has been added, to give a compound of formula (11)

(11)

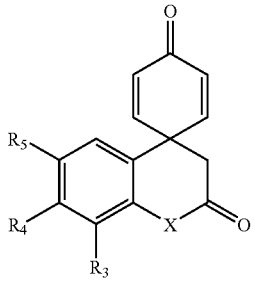

which is reacted with an amine of formula $NHR_6$ where $R_6$ is as defined in claim 1 to give, by opening of the lactone, the corresponding amide of formula (12)

(12)

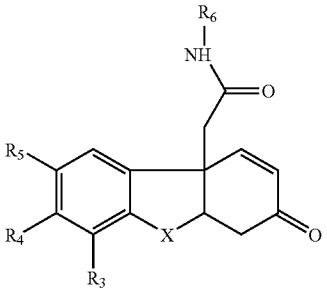

which is cyclized to give a compound of formula (1a), (1a)

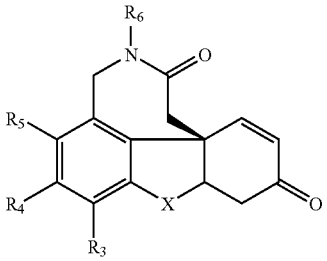

which is optionally subjected to a diastereoselective reduction to give the corresponding derivative of formula (1b), (1b)

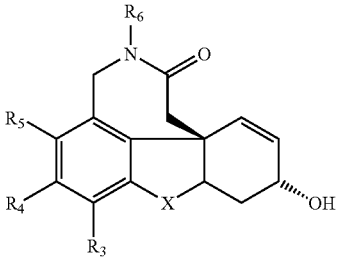

whose amide function can optionally be reduced to give a compound of formula (1c)

(1c)

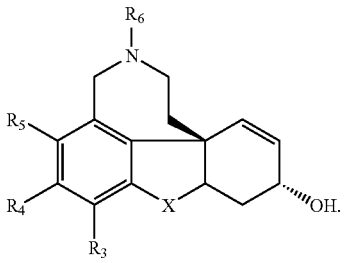

6. A method according to claim 5, characterized in that the compound of formula (12) is resolved and then the synthesis is continued to give the compounds of formula (1a) to (1c) in their optically active forms.

7. A method according to claim 5, characterized in that the compound of formula (1a) is resolved and then the synthesis is continued to give the compounds of formula (1b) to (1c) in their optically active forms.

8. A method according to claim 1, characterized in that galanthamine is prepared in the form of the racemate or of its optically pure isomers.

9. Compound of formula (11)

(11)

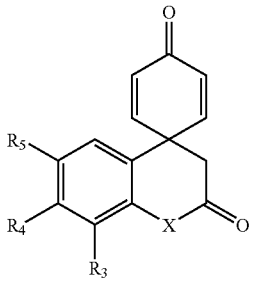

in which $R_3$, $R_4$ and $R_5$ represent each independently of one another a hydrogen atom, a hydroxyl group or a $(C_1–C_{12})$ alkoxy group and X represents alternatively an oxygen atom or a sulfur atom or an —SO group or an $—SO_2$ group or a group $—NR_6$ where $R_6$ represents a hydrogen atom, a $(C_1–C_{12})$alkyl group, a group $—(CH_2)_nNR_7R_8$ or a group $—(CH_2)_nN^+R_7R_8R_9$ where n=1 to 12, $R_7$ and $R_8$ represent each independently of one another a hydrogen atom; a cyano; $(C_1–C_4)$alkyl; aryl$(C_1C_4)$alkyl; aryl$(C_1–C_4)$alkenyl; $(C_1–C_4)$alkyl-carbonyl or arylcarbonyl radical; the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals; or represents an amine-protective group.

10. Compounds according to claim 9, characterized in that $R_3=OCH_3$, $R_4=R_5=H$ and X=O, NH or $N—CH_3$.

11. Compound of formula (8)

(8)

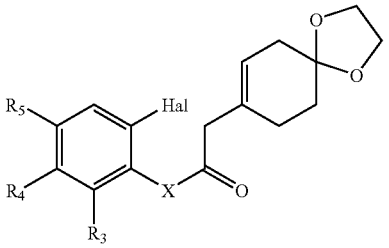

in which Hal represents a halogen atom selected from bromine and iodine atoms, and $R_3$, $R_4$, and $R_5$ represent each independently of one another a hydrogen atom, a hydroxyl group or a $(C_1–C_{12})$alkoxy group; and X represents alternatively *an oxygen atom or* a sulfur atom or a nitrogen atom or an —SO group, an $—SO_2$ group or a group $—NR_6$ where $R_6$ represents a hydrogen atom, a $(C_1–C_{12})$alkyl group, a group $—(CH_2)_nNR_7R_8$ or a group $—(CH_2)_nN^+R_7R_8R_9$ where n=1 to 12, $R_7$ and $R_8$ represent each independently of one another a hydrogen atom; a cyano; $(C_1–C_4)$alkyl; aryl $(C_1–C_4)$alkyl; aryl$(C_1–C_4)$alkenyl; $(C_1–C_4)$alkyl-carbonyl or arylcarbonyl radical; the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals; or represents an amine-protective group.

12. Compounds according to claim 11, characterized in that Hal=I, $R_3=OCH_3$, $R_4=R_5=H$ and X=NH or $N—CH_3$.

13. Compound of formula (12)

(12)

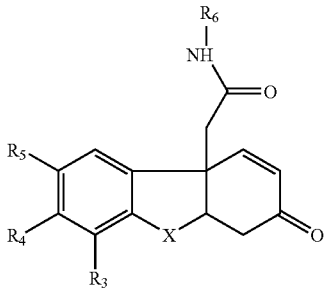

in which $R_3$, $R_4$ and $R_5$ represent each independently of one another a hydrogen atom, a hydroxyl group or a $(C_1–C_{12})$ alkoxy group; and $R_6$ represents a hydrogen atom, a $(C_1–C_{12})$alkyl group, a group $—(CH_2)_nNR_7R_8$ or a group $—(CH_2)_nN^+R_7R_8R_9$ where n=1 to 12, $R_7$ and $R_8$ represent each independently of one another a hydrogen atom; a cyano; $(C_1–C_4)$alkyl; aryl$(C_1–C_4)$alkyl; aryl$(C_1–C_4)$alkenyl; $(C_1–C_4)$alkyl-carbonyl or arylcarbonyl radical; the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals; and X represents alternatively an oxygen atom or a sulfur atom or an —SO group or an $—SO_2$ group or a group $—NR_6$ where $R_6$ is as defined above or represents an amine-protective group.

14. Compound of formula (9)

(9)

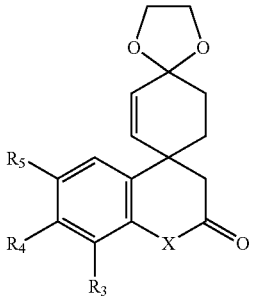

in which Hal, $R_3$, $R_4$, and $R_5$ are as defined in claim 1 and X represents alternatively *an oxygen atom or* sulfur atom or a nitrogen atom or an —SO group, an —$SO_2$ group or a group —$NR_6$ where $R_6$ represents a hydrogen atom, a ($C_1$–$C_{12}$) alkyl group, a group —$(CH_2)_n NR_7R_8$ or a group —$(CH_2)_n N^+R_7R_8R_9$ where n=1 to 12, $R_7$ and $R_8$ represent each independently of one another a hydrogen atom; a cyano; ($C_1$–$C_4$) alkyl; aryl($C_1$–$C_4$)alkyl; aryl($C_1$–$C_4$)alkenyl; ($C_1$–$C_4$)alkylcarbonyl or arylcarbonyl radical; the alkyl, alkenyl, and aryl radicals being optionally substituted by one or more identical or different radicals selected from halo, hydroxyl, alkoxy, alkylthio, acyl, free, salt-form or esterified carboxyl, cyano, nitro, mercapto or amino radicals, the amino radical being itself optionally substituted by one or more identical or different alkyl radicals; or represents an amine-protective group.

15. The process of claim 2 wherein said support is an inorganic support.

*16. A compound according to claim 11 as follows:*

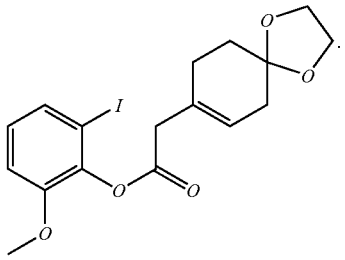

*17. A compound according to claim 14 as follows:*

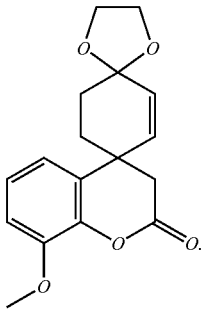

* * * * *

UNITED STATES PATENT AND TRADEMARK OFFICE

CERTIFICATE OF CORRECTION

PATENT NO. : RE41,366 E
APPLICATION NO. : 12/283904
DATED : June 1, 2010
INVENTOR(S) : Claude Thal et al.

It is certified that error appears in the above-identified patent and that said Letters Patent is hereby corrected as shown below:

At column 23, line 17, before "sulfur" insert --a--.

Signed and Sealed this
Twenty-fourth Day of May, 2011

David J. Kappos

David J. Kappos
*Director of the United States Patent and Trademark Office*

UNITED STATES PATENT AND TRADEMARK OFFICE

CERTIFICATE OF CORRECTION

PATENT NO. : RE41,366 E
APPLICATION NO. : 12/283904
DATED : June 1, 2010
INVENTOR(S) : Claude Thal et al.

It is certified that error appears in the above-identified patent and that said Letters Patent is hereby corrected as shown below:

On the cover page, under (30) Foreign Application Priority Data, (JP) should read (FR)

Signed and Sealed this
Eighth Day of May, 2012

David J. Kappos

David J. Kappos
*Director of the United States Patent and Trademark Office*